United States Patent [19]

Mizuta et al.

[11] 4,115,699

[45] Sep. 19, 1978

[54] APPARATUS FOR SENSITIVE DETECTION AND QUANTITATIVE ANALYSIS OF BIOLOGICAL AND BIOCHEMICAL SUBSTANCES

[75] Inventors: Toshinobu Mizuta, Takasaki; Tooru Hayashi, Tokyo, both of Japan

[73] Assignee: Kabushiki Kaisha Nihon Kotai Kenkyujo, Japan

[21] Appl. No.: 807,153

[22] Filed: Jun. 16, 1977

[51] Int. Cl.² ............................................. G01N 21/38
[52] U.S. Cl. .................................................. 250/461 B
[58] Field of Search ............................ 250/461 B, 573; 356/114

[56] References Cited

U.S. PATENT DOCUMENTS

| | | | |
|---|---|---|---|
| 3,886,363 | 5/1975 | Ohnishi et al. | 250/461 B |
| 3,967,902 | 7/1976 | Steinberg | 356/114 |

*Primary Examiner*—Davis L. Willis
*Attorney, Agent, or Firm*—Oblon, Fisher, Spivak, McClelland & Maier

[57] ABSTRACT

Apparatus is disclosed for sensitively detecting and quantitatively analyzing biological and biochemical substances. Charged into a cell is a test molecule labeled with a fluorescent dyestuff. An exciting optical system transmits plane polarized light from a light source into the labeled molecule to excite the molecule, and a polarizing optical system takes up fluorescent light emitted from the molecule. A photomultiplier is arranged to measure the fluorescence intensities of parallel and perpendicularly polarized light from the molecule. A calculator coordinated with the polarizing optical system computes and converts the fluorescence intensities into the degree of polarization of the molecule.

3 Claims, 2 Drawing Figures

APPARATUS FOR SENSITIVE DETECTION AND QUANTITATIVE ANALYSIS OF BIOLOGICAL AND BIOCHEMICAL SUBSTANCES

BACKGROUND OF THE INVENTION

1. Field of the Invention

The present invention relates to an apparatus for sensitively detecting and quantitatively analyzing biological and biochemical substances.

2. Description of the Prior Art

With the recent progress of immunology, the application of immunity has become important and widespread. In most immunological measurement methods, the very specific nature of an antigen-antibody reaction is utilized to selectively detect any elusive substances. Diagnoses in syphilis, typhoid fever, paratyhoid, viruses, hormones or other biochemically active molecules and their binding proteins or receptors on cells, tumor antigens-antibodies, enzymes and inhibitors and the like to which such immunological measurement methods have been applied. In such known methods, however, the antigen-antibody reaction is determined by observing with naked eye any specific changes in precipitation and agglutination of the reaction. The prior art techniques are tedious and time-consuming because an inspector must have much experience and high concentration in visually observing the antigen-antibody reaction. Another problem resides in inaccurate observation of that reaction arising from the inspector's preference.

SUMMARY OF THE INVENTION

Therefore, it is an object of the invention to eliminate the above difficulties noted by the existing techniques.

Another object of the invention is to provide an apparatus for sensitively detecting and quantitatively analyzing biological and biochemical substances with utmost ease and greatest exactness and in an extremely short length of time.

These and objects of the invention as will hereinafter become clear have been obtained by providing an apparatus for detecting and analyzing biological and biochemical substances wherein the degree of fluorescence depolarization of an antigen or antibody molecule labeled with a fluorescent dyestuff can quantitatively be calculated by electrical determination of any change in the Brownian movement of the labeled molecule.

For reducing into practice the apparatus of the invention, the labeled molecule is excited by plane polarized light, and the fluorescence intensities of the labeled molecule are obtained at electric vectors parallel with the plane of incidence and perpendicularly with the plane of incidence on a photomultiplier. The degree of depolarization is then computed by way of a calculator which is coordinated with the photomultiplier. The apparatus according to the invention is so configured that the labeled molecule can be sensitively detected and quantitatively analyzed, with its progressive changes observed, by calculating the degrees of polarization prior to and after the reaction of the labeled molecule.

Having generally described the invention, a furthter understanding can be made by reference to the detailed description and the accompanying sheets of drawings incorporating the principles of this invention which is provided only for purposes of illustration and not intended to be construed as limiting unless otherwise described.

DETAILED DESCRIPTION OF THE INVENTION

One preferred embodiment of an apparatus 10 according to the invention will now be described as applied to an immunological measurement method employing the specificity of an antigen-antibody reaction.

Figure 1:
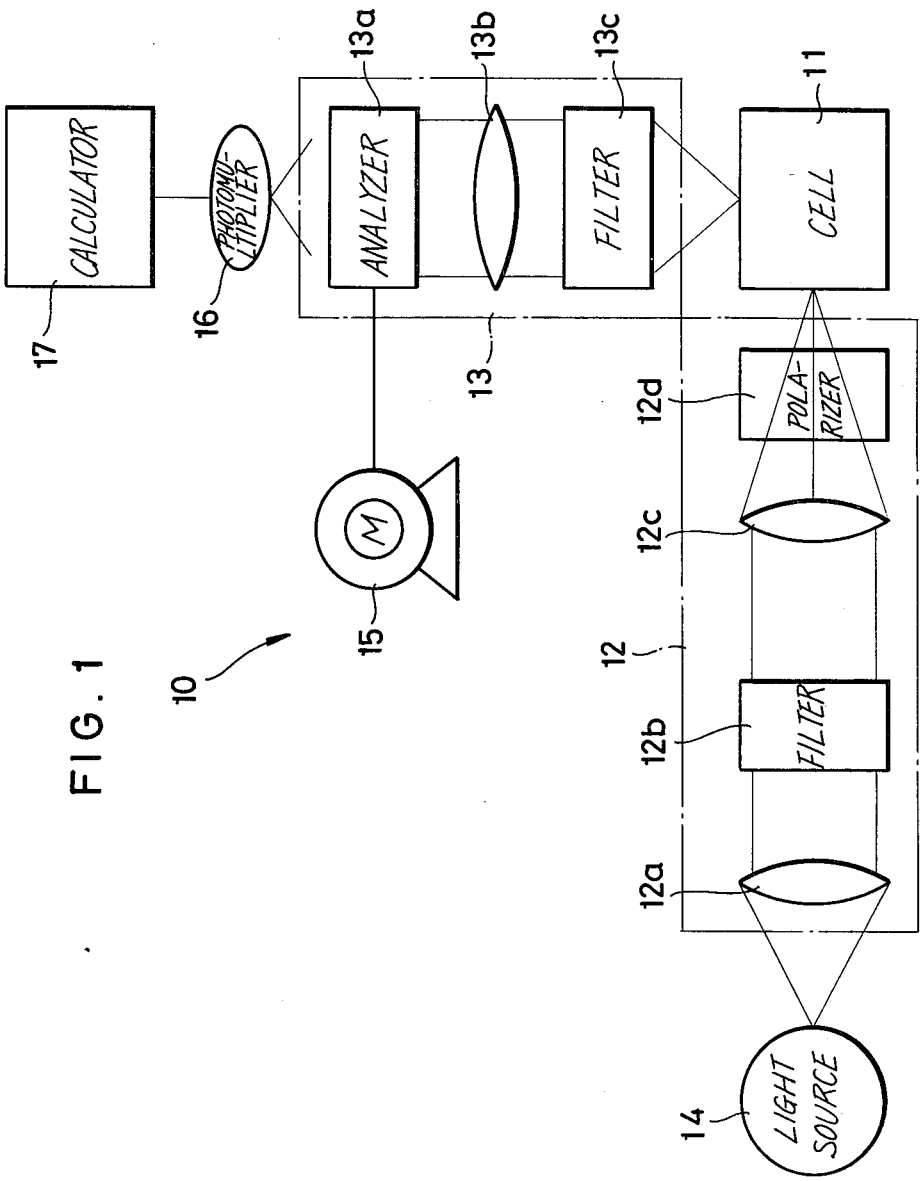
FIG. 1 is a block diagram explanatory of the principles of an apparatus according to the invention.

In FIG. 1 there is shown a cell 11 for accommodating therein a sample molecule such as an antigen which is labeled with a fluorescent dyestuff. Designated at 12 is an exciting optical system which is oriented in a lateral or X-axis direction relative to the cell 11 and which excites the labeled molecule within the cell 11. A polarizing optical system 13 is arranged in a vertical or Y-axis direction relative to the cell 11 and substantially at a right angle to the X-axis, and gathers parallel and perpendicularly polarized light coming from the excited molecule.

The exciting optical system 12 comprises a lens 12a which transforms fluorescent light transmitted elliptically from a light source 14 to plane fluorescent light, and a filter 12b which allows for transmission of only monochromatic light with a desired wavelength out of the plane fluorescent light passing through the lens 12a. Placed within the exciting optical system 12 are a lens 12c for collecting the monochromatic light from the lens 12b. The perpendicularly polarized light generating from a polarizer 12d of the exciting optical system 12 is caused to irradiate the labeled molecule contained in the cell 11, thereby exciting the molecule.

The light source 14 lies in opposite relation to the cell 11 in the X-axis direction and includes, as for example, a tungsten lamp.

The polarizer 12d includes, as for example, Glan-Thomonsche prisms, Rochon's prisms and Nicol's prisms formed of monoaxial crystallines such as crystal and calcite, reflections by the surface of separation of dielectrics and the like.

Figure 2:
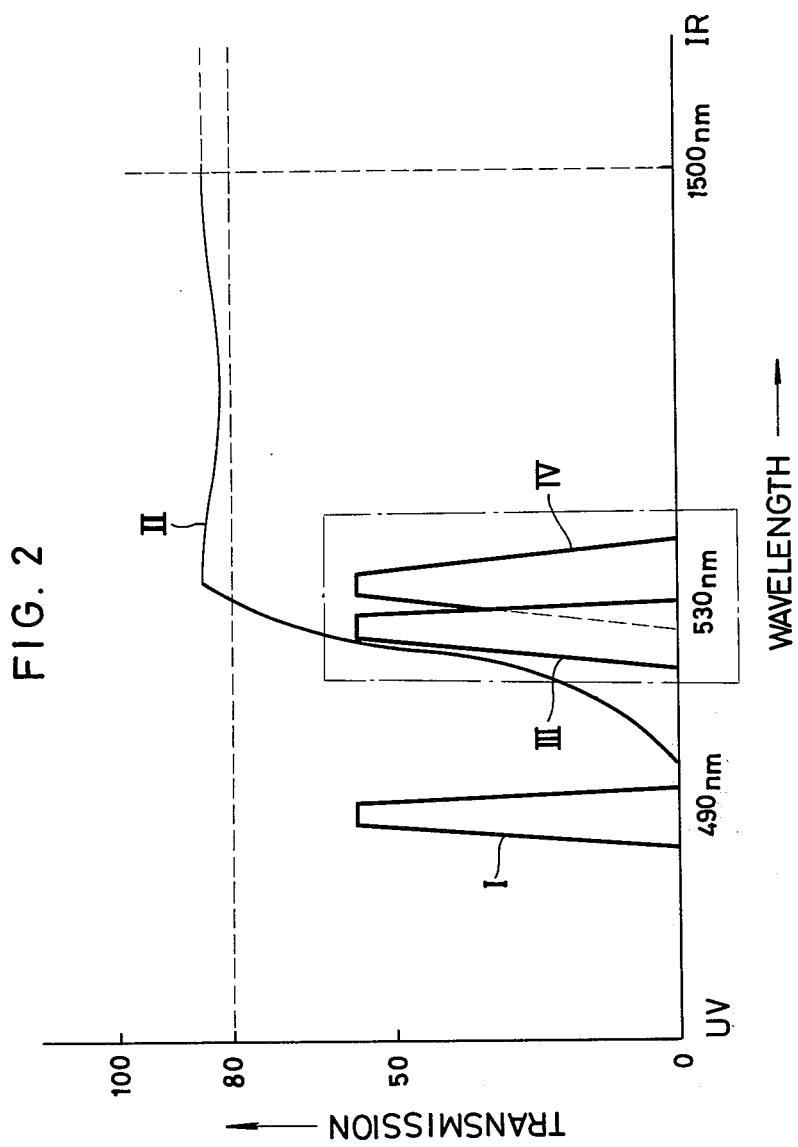
FIG. 2 is a view showing the spectrum characteristics of the filters used for the optical systems of the apparatus.

The monochromatic light transmitted from the filter 12b exhibits a spectrum at a wavelength of 490mm as shown at I in FIG. 2.

The polarizing optical system 13 comprises a filter 13c which transmits only light emitted by the sample molecule in the cell 11, a lens 13b serving to collect the fluorescent light from the cut-off filter 13c, and an analyzer 13a for gathering the fluorescent light from the sample molecule. Arranged further is an electric motor 15 with a speed of about 4 rpm/sec for connection to the analyzer 13a.

In this arrangement the analyzer 13a, when rotated by the motor 15, takes up parallel and perpendicularly polarized light from the tested molecule for measurement of its fluorescence intensities and subsequent conversion by a photomultiplier 16 into an electrical signal. The signal is then caused to enter a calculator 17 so that the molecule can be detected and analyzed to determine whether or not the molecule has provided any reaction.

For sensitive detection of an antigen-antibody reaction according to the apparatus 10 of the invention, a test antigen or antibody is first labeled with a fluorescent dyestuff which can be selected, for example, from fluorescent isothiocyanate, tetramethylrhodamine isothiocyanate and the like. The antigen or antibody labeled with the fluorescent dyestuff is fed to the cell 11 and is then subjected to irradiation and excitation by plane polarized light which is obtained by passing the monochromatic light from the light source 14 through the exciting optical system 12. The thus excited molecule in the antigen or antibody emits fluorescent light, with occurrence of the random Brownian movement. Parallel and perpendicularly polarized light is taken out of the fluorescent light of the molecule with the use of the analyzer 13a driven by the motor 15, and is transmitted to the photomultiplier 16 where the fluorescence intensities of both the parallel polarized light and the perpendicularly polarized light are calculated. Under the assumption that the fluorescence intensity of the perpendicularly polarized light and that of the parallel polarized light are $I_1$ and $I_2$, respectively, the degree of polarization P is expressed by equation (1).

$$P = \frac{I_2 - I_1}{I_2 + I_1} \quad (1)$$

As is well known in the art as the degree of depolarization by the Brownian movement, the degree of polarization P in which the labeled molecule is under the Brownian movement is lower than the degree of polarization Po in which the labeled molecule is in stationary condition. The degree of depolarization may be written as a function of both the fluorescence life $\tau$ of the labeled molecule and the rotational relaxation time $\pi$ of the labeled molecule. Thus, the relationship between Po/P and $\tau/\pi$ is defined by equation (2).

$$\frac{Po}{P} = 1 + A\left(\frac{\tau}{\rho}\right) \quad (2)$$

The coefficient A in equation (2) is variable, depending on any optical systems employed to calculate any degrees of polarization. For instance, A = 3 — Po in the optical system where an labeled antigen or antibody molecule is excited by plane polarized light. In the case where a labeled antigen or antibody molecule is of a spherical particle in solution, the rotational relaxation time $\pi o$ of the labeled molecule by the Brownian movement becomes equation (3).

$$\frac{1}{\rho o} = \frac{kT}{3Vo\eta} \quad (3)$$

where Vo is the volume of the spherical particle, $\eta$ is the solvent viscosity, T is the absolute temperature, and k is Boltzmann's constant.

Substitution of equation (3) for equation (2) gives equation (4) which is generally called as the Perrin-Levshin formula.

$$\frac{Po}{P} = 1 + A\frac{kT}{3Vo\eta}\tau \quad (4)$$

With an increase in solvent viscosity and molecule volume, and with a decrease in solvent temperature, the degree of polarization derived from the molecule in solution becomes high. The limiting value of Po is found to be substantially equal to the degree of polarization as calculated when the Brownian movement is completely depressed.

From the foregoing consideration, it is understood that when any other molecule such as a specific antigen or antibody is brought into contact with the labeled antigen or antibody molecule, the labeled molecule increases in its molecular weight, thereby resulting in prolonged rotational relaxation time and increased degree of polarization. In contrast to the case where the labeled antigen or antibody is taken individually, the fluorescence intensities of parallel and perpendicularly polarized light of the antigen-antibody complex as measured in the same manner described hereinabove are varied since the labeled molecule increases in it molecular weight, and hence, the Brownian movement is depressed. More particularly, in view of the fact that any increase in the degree of polarization P in equation 1 means that an antigen-antibody reaction has occurred, sensitive detection can be easily made to determine if there exists an antigen or antibody molecule in the tested specimen contained in the cell 11 of the apparatus 10.

If the tested molecules produces, by intrusion of any foreign matter, scattered light which would otherwise cause operational inconveniences, the filter 13c of the polarizing optical system 13 may be replaced by any suitable filter possessing spectrum characteristics at a wavelength of 530mm. This condition is best illustrated at II, III or IV in FIG. 2.

For quantitative analysis of an antigen-antibody reaction by means of the apparatus 10 according to the invention, a labeled antigen having a specific degree of polarization Po is placed at a concentration Co together with a certain amount of an unlabeled antibody so that the antigen-antibody complex is formed as having a degree of polarization of $P_1$ and a concentration $C_2$. The degree of polarization Pm of the resultant mixed solution of the labeled antigen-antibody complex is expressed by equation (5)

$$Pm = \frac{(Co - C_1)Po + C_1 P_2}{Co} \quad (5)$$

Using equation (5), the concentration of the antibody as $C_1$ is determined from the measured value of Pm with the already known values of Co, Po and $P_1$. The degree of polarization Pm is measured by the analyzer 16, and may preferably be read on a digital display and printed on a recording chart.

Advantageously, an extremely short length of time of 60 seconds is sufficiently possible for each measurement of an antigen-antibody reaction. Another advantage is that a sample to be charged into the cell is in a very limited amount ranging from 1 μl to 10 μl.

It is of interest to note that those characteristic features make the apparatus of the invention significantly effective and widely applicable. Some representative examples of usage are as follows:
  (1) Antigen-Antibody reactions
  (2) Hormone-binding protein interactions
  (3) Enzymes, coenzymes and inhibitors-substrates
  (4) Measurement of viscosity of solutions with free fluorescein
  (5) Molecular weight determination of globular proteins after fluorescein conjugation
  (6) Receptors for hormones
  (7) Receptors for immunoglobulin on cell surface (8) Cellular fluidity
(9) Cell membrane fluidity
(10) Assay of complement systems
(11) Liver enzymes in blood plasma
(12) Serum proteins Having fully described the invention, it will be apparent to one of ordinary skill in the art that many changes and modifications can be made thereto without departing from the spirit or scope of the invention as set forth herein.

What is claimed as new and intended to be covered by letters patent is:

1. Apparatus for sensitively detecting and quantitatively analyzing biological and biochemical substances, which apparatus comprises: a cell for accommodating therein a test molecule labeled with a fluorescent dyestuff; an exciting optical system oriented in an X-axis or vertical direction relative to said cell for transmitting plane polarized light to excite said labeled molecule, said exciting optical system including a lens for transforming plane light originating from a light source placed in opposite relation to said cell in the X-axis direction, a filter for transmitting only monochromatic light out of the light passing through said lens, and a lens for collecting the monochromatic light from said transforming lens; a polarizing optical system oriented in a Y-axis or lateral direction relative to said cell for taking up fluorescent light emitted from said labeled molecule, said polarising optical system including a filter and a lens each for transmitting the fluorescent light only, and an analyzer for collecting parallel and perpendicularly polarized light from said molecule; a photomultiplier for measuring the fluorescence intensities of the parallel and perpendicularly polarized light; and a calculator for computing and converting the fluorescence intensities into the degree of polarization of said molecule.

2. Apparatus as defined in claim 1 wherein said transmission filter of said exciting optical system has spectrum characteristics at a wavelength of 490mm.

3. Apparatus as defined in claim 1 wherein said transmission filter of said polarizing optical system has spectrum characteristics at a wavelength of 530mm.

* * * * *